(12) United States Patent
Bai et al.

(10) Patent No.: US 9,266,852 B2
(45) Date of Patent: Feb. 23, 2016

(54) DAIDZEIN DERIVATIVE, PHARMACEUTICALLY ACCEPTABLE SALT AND PREPARATION METHOD THEREOF, AND PHARMACEUTICAL COMPOSITION CONTAINING SAME

(71) Applicant: ANHUI BIOCHEM BIO-PHARMACEUTICAL CO., LTD, Hefei, Anhui (CN)

(72) Inventors: Jun Bai, Hefei (CN); Caiyue Shen, Hefei (CN); Shigao Hu, Hefei (CN)

(73) Assignee: Anhui Biochem Bio-Pharmaceutical Co., Ltd, Anhui (CN)

( * ) Notice: Subject to any disclaimer, the term of this patent is extended or adjusted under 35 U.S.C. 154(b) by 0 days.

(21) Appl. No.: 14/362,890

(22) PCT Filed: Nov. 28, 2012

(86) PCT No.: PCT/CN2012/085452
§ 371 (c)(1),
(2) Date: Jun. 4, 2014

(87) PCT Pub. No.: WO2013/083014
PCT Pub. Date: Jun. 13, 2013

(65) Prior Publication Data
US 2014/0336247 A1    Nov. 13, 2014

(30) Foreign Application Priority Data
Dec. 6, 2011  (CN) ........................ 2011 1 0401307

(51) Int. Cl.
*C07D 311/00*   (2006.01)
*C07D 311/36*   (2006.01)
*A61K 31/352*   (2006.01)
*A61K 9/19*     (2006.01)

(52) U.S. Cl.
CPC ................ *C07D 311/36* (2013.01); *A61K 9/19* (2013.01); *A61K 31/352* (2013.01)

(58) Field of Classification Search
CPC ........................... C07D 311/36; C07D 305/30
USPC ................................................... 549/403, 401
See application file for complete search history.

(56) References Cited

U.S. PATENT DOCUMENTS 6,121,010 A * 9/2000 Vallee et al. .................... 435/26
2005/0124678 A1  6/2005 Levy et al.

FOREIGN PATENT DOCUMENTS

CN         1449763 A      10/2003
CN       101659648 A       3/2010

OTHER PUBLICATIONS

Qui et al, Chem. Abs. DN 146:62680 RN 868584-37-6 (2006).*

* cited by examiner

*Primary Examiner* — Andrew D Kosar
*Assistant Examiner* — Raymond Covington
(74) *Attorney, Agent, or Firm* — Lewis Roca Rothgerber Christie LLP

(57) ABSTRACT

Disclosed is a daidzein derivative as represented by formula (I), or pharmaceutically acceptable salt thereof. Compared to the daidzein in the prior art, the daidzein derivative hydrochloride, in particular to the 7-O—N,N-diethyl-aminoacetyl daidzein hydrochloride, prepared by the daidzein derivative of the present invention, has better solubility and effect for treating cardiovascular diseases.

40 Claims, No Drawings

DAIDZEIN DERIVATIVE, PHARMACEUTICALLY ACCEPTABLE SALT AND PREPARATION METHOD THEREOF, AND PHARMACEUTICAL COMPOSITION CONTAINING SAME

CROSS-REFERENCE TO RELATED APPLICATION(S)

This application is a National Phase Patent Application and claims priority to and benefit of International Application Number PCT/CN2012/085452, filed on Nov. 28, 2012, which claims priority to and benefit of Chinese Patent Application Number 201110401307.9, filed on Dec. 6, 2011, the entire disclosures of which are incorporated herein by reference.

TECHNICAL FIELD

The present invention relates to the field of pharmaceutical chemistry, and in particular to a daidzein derivative, pharmaceutically acceptable salt thereof, preparation method thereof and pharmaceutical use of the compound for resisting cardiovascular diseases.

BACKGROUND OF THE INVENTION

Cardiovascular diseases, also known as circulatory system diseases, are a series of diseases caused by heart and vascular lesions. Specific symptoms of cardiovascular diseases include heart disease, hypertension and hyperlipidemia, etc. The cardiovascular disease is a serious disease hazarding human health and has become the second killer after the cancer. Moreover, tens of thousands of people become disabled due to suffering from the cardiovascular disease every year.

Currently, the drug of isoflavones is a comparatively important kind of drug among drugs for treating cardiovascular diseases. Studies have shown that the drug of isoflavones not only has effects of dilating coronary artery, femoral artery and cerebral artery, but also has various efficacies such as increasing cerebral blood flow, strengthening blood circulation in the limbs, lowering blood viscosity, weakening vascular resistance, reducing myocardial oxygen consumption, improving cardiac function, enhancing microcirculation, strengthening peripheral blood flow, changing blood rheology, reducing blood pressure and improving heart rate and so on.

Puerarin and daidzein are representatives in these drugs of isoflavones, however, limited by natural resources, the yield of the puerarin and daidzein extracted naturally is lower and the purity of the product is poor. In addition, the two drugs are difficult to be absorbed by the human body due to their poor water solubility, thereby resulting in low bioavailability.

Although U.S. Pat. No. 6,121,010A discloses 7-O—N,N-dimethyl-aminobutyryl daidzein, the compound only functions as an enzyme system inhibitor of certain neurotransmitters (such as 5-HT and DA), which is used to inhibit the acetaldehyde (which is formed by metabolism of 5-HT or DA through a monoamine oxidase) from being oxidized, and used for the treatment of alcohol dependence and alcohol abuse, the patent does not relate to the use of the compound for the treatment of cardiovascular diseases.

SUMMARY OF THE INVENTION

In order to solve the above problems, an object of the present invention is to provide a novel compound which can be used for treating cardiovascular diseases, compared with the prior art, the novel compound has a higher solubility and better therapeutic effect for cardiovascular diseases.

Another object of the present invention is to provide a method for preparing the compound.

A yet another object of the present invention is to provide a pharmaceutical composition comprising the compound.

A still another object of the present invention is to provide a pharmaceutical use of the compound and the pharmaceutical composition.

The technical solutions of the present invention are as follows.

In one aspect, the present invention provides a daidzein derivative having a structure represented by formula (I) or pharmaceutically acceptable salt thereof:

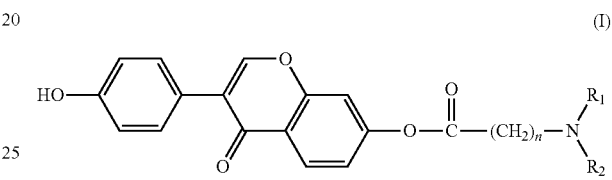

Wherein, $R_1$ and $R_2$ are each independently H, substituted or unsubstituted $C_{1-10}$ alkyl, or $R_1$ and $R_2$ together with the attached N atom form substituted or unsubstituted 5-10 membered heterocyclic group, and when substituted, the $C_{1-10}$ alkyl or 5-10 membered heterocyclic group has a substitute of $C_{1-10}$ alkyl, hydroxyl, carboxyl or halogen; n is 0, 1, 2, 3, 4 or 5; and the daidzein derivative does not comprise 7-O—N,N-dimethyl-aminobutyryl daidzein.

Preferably, $R_1$ and $R_2$ are each independently H, substituted or unsubstituted $C_{1-10}$ alkyl, wherein when substituted, the $C_{1-10}$ alkyl has a substitute of hydroxyl, carboxyl or halogen;

Further preferably, $R_1$ and $R_2$ are each independently H or unsubstituted $C_{1-10}$ alkyl; wherein the $C_{1-10}$ alkyl is preferably $C_{1-6}$ alkyl, and more preferably $C_{1-4}$ alkyl.

Preferably, n is 1, 2 or 3.

According to the specific embodiments of the present invention, the $C_{1-4}$ alkyl is for example methyl, ethyl, propyl, isopropyl, butyl, isobutyl, t-butyl, pentyl, hexyl or heptyl; 5-10 membered heterocyclic group is for example pyrrolidinyl, piperidinyl or morpholinyl.

The present invention further provides a pharmaceutically acceptable salt of the daidzein derivative having a structure represented by formula (I). The pharmaceutically acceptable salt is a salt formed by the daidzein derivative having a structure represented by formula (I) and an organic acid or inorganic acid; preferably, the organic acid is selected from the group consisting of acetic acid, trifluoroacetic acid, methane sulfonic acid, toluene sulfonic acid, maleic acid, succinic acid, tartaric acid, citric acid or fumaric acid; the inorganic acid is selected from the group consisting of hydrochloric acid, hydrobromic acid, nitric acid, sulfuric acid or phosphoric acid.

According to the specific embodiments of the present invention, the daidzein derivative has a structure as shown in formula (II):

(II)

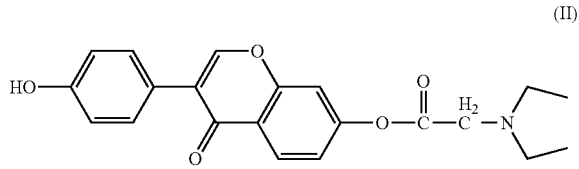 [SMILES: CCN(CC)CC(=O)Oc1ccc2c(=O)c(-c3ccc(O)cc3)coc2c1]

the pharmaceutically acceptable salt is a hydrochloride having a structure as shown in formula (III):

(III)

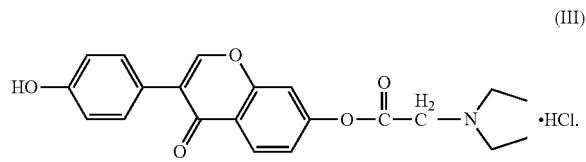

In another aspect, the present invention further provides a method for preparing the daidzein derivative or pharmaceutically acceptable salt thereof, the method comprises the following steps:

a) reacting daidzein and halogenated alkyl acyl halide to obtain halogenated alkyl acyl daidzein:

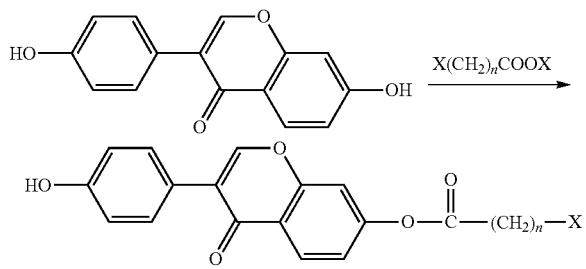

wherein X is F, Cl, Br or I;

b) reacting the halogenated alkyl acyl daidzein and amine represented by formula (IV) to obtain a daidzein derivative:

(IV)

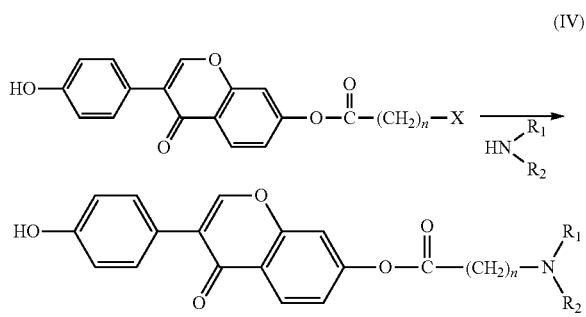

and c) optionally, converting the daidzein derivative into its pharmaceutically acceptable salt;

$R_1$, $R_2$ and n are defined as above.

Wherein the step a) specially comprises:

reacting daidzein and halogenated alkyl acyl halide with pyridine as a catalyst in a first organic solvent to obtain halogenated alkyl acyl daidzein.

Preferably, the first organic solvent is an organic solvent of alcohols, halogenated hydrocarbons, ethers, ketones or esters, or a mixture thereof; wherein the organic solvent of alcohols is selected from one or more of the group consisting of methanol, ethanol, isopropanol, n-propanol, n-butanol and t-butanol; the organic solvent of halogenated hydrocarbons is selected from one or more of the group consisting of dichloromethane, chloroform and 1,2-dichloroethylene; the organic solvent of ethers is selected from one or more of the group consisting of tetrahydrofuran, diethyl ether, isopropyl ether, anisole and methyl tertiary butyl ether; the organic solvent of ketones is selected from one or more of the group consisting of acetone, methyl isobutyl ketone, butanone and methyl n-butyl ketone; the organic solvent of esters is selected from one or more of the group consisting of ethyl acetate, isobutyl acetate, butyl acetate and isopropyl acetate; more preferably, the first organic solvent is acetone;

According to the present invention, during the reaction of the daidzein and halogenated alkyl acyl halide, the reaction temperature is 0° C.-25° C., further preferably 1° C.-15° C. and more preferably 2° C.-5° C.; the reaction time is preferably 1 h-10 h, further preferably 2 h-8 h and more preferably 3 h-7 h.

The mass ratio of the first organic solvent and pyridine is not particularly limited in the present invention. The mass ratio of the daidzein and halogenated alkyl acyl halide is 1:10-2:5, and further preferably 1:8-3:6. The concentration of the daidzein in the first organic solvent is not particularly limited in the present invention, and the concentration of the daidzein in the first organic solvent is preferably 0.05 mol/l-0.2 mol/l, further preferably 0.08 mol/l-0.18 mol/l, more preferably 0.09 mol/l-0.15 mol/l, and most preferably 0.1 mol/l-0.12 mol/l.

According to the present invention, after the halogenated alkyl acyl daidzein is obtained through the above reaction, the reaction product is filtered, washed and dried. The operations of filtrating, washing and drying can be performed according to the method well known to those skilled in the art, which are not particularly limited in the present invention. The obtained halogenated alkyl acyl daidzein can be further purified according to the recrystallization method well known to those skilled in the art.

According to the present invention, in the step b), the halogenated alkyl acyl daidzein further reacts with the amine corresponding to

to prepare the daidzein derivative, the step b) specifically comprises:

dissolving the halogenated alkyl acyl daidzein obtained in the step a) in a second organic solvent, adding potassium carbonate and potassium iodide, and then adding

heating to reflux, to obtain the daidzein derivative through reaction.

Preferably, the second organic solvent is an organic solvent of alcohols, halogenated hydrocarbons, ethers, ketones or esters, or a mixture thereof; wherein the organic solvent of alcohols is selected from one or more of the group consisting of methanol, ethanol, isopropanol, n-propanol, n-butanol and t-butanol; the organic solvent of halogenated hydrocarbons is selected from one or more of the group consisting of dichloromethane, chloroform and 1,2-dichloroethylene; the organic solvent of ethers is selected from one or more of the group consisting of tetrahydrofuran, diethyl ether, isopropyl ether, anisole and methyl tertiary butyl ether; the organic solvent of ketones is selected from one or more of the group consisting of acetone, methyl isobutyl ketone, butanone and methyl n-butyl ketone; the organic solvent of esters is selected from one or more of the group consisting of ethyl acetate, isobutyl acetate, butyl acetate and isopropyl acetate; further preferably, the second organic solvent is identical to the first organic solvent in the step a); more preferably, the second organic solvent is acetone.

According to the present invention, the time for reflux reaction is preferably at least 1 h, more preferably at least 2 h, and most preferably at least 3 h.

After the daidzein derivative is obtained through the above reaction, the mixture after the reaction is cooled to room temperature, filtered, washed and concentrated. Preferably, after concentration, the obtained product is added with acetone to distill, and then washed with anhydrous ethanol, followed by dried with anhydrous sodium sulfate.

The present invention further provides a pharmaceutically acceptable salt of daidzein, preferably hydrochloride. According to the present invention, in the step c), the obtained daidzein derivative can be used to prepare a hydrochloride of the daidzein derivative, the step c) specifically comprises:

dissolving the daidzein derivative obtained in the step b) in a third organic solvent, then adding an organic or inorganic acid, so that the daidzein derivative can react with the acid to form a pharmaceutically acceptable salt of the daidzein derivative; then the salt may be obtained through filtration and concentration.

Preferably, dissolving the daidzein derivative obtained in the step b) in a third organic solvent, and then passing dry HCl gas or adding hydrochloric acid, and performing filtration and concentration to obtain a hydrochloride of the daidzein derivative.

Wherein the third organic solvent is an organic solvent of alcohols, halogenated hydrocarbons, ethers, ketones or esters, or a mixture thereof; wherein the organic solvent of alcohols is selected from one or more of the group consisting of methanol, ethanol, isopropanol, n-propanol, n-butanol and t-butanol; the organic solvent of halogenated hydrocarbons is selected from one or more of the group consisting of dichloromethane, chloroform and 1,2-dichloroethylene; the organic solvent of ethers is selected from one or more of the group consisting of tetrahydrofuran, diethyl ether, isopropyl ether, anisole and methyl tertiary butyl ether; the organic solvent of ketones is selected from one or more of the group consisting of acetone, methyl isobutyl ketone, butanone and methyl n-butyl ketone; the organic solvent of esters is selected from one or more of the group consisting of ethyl acetate, isobutyl acetate, butyl acetate and isopropyl acetate; further preferably, the third organic solvent is identical to the first organic solvent in the step a); more preferably, the third organic solvent is methanol.

According to the present invention, the pharmaceutically acceptable salt of the daidzein derivative obtained may also be recrystallized according to the method well known to those skilled in the art to perform further purification.

In yet another aspect, the present invention provides a pharmaceutical composition comprising the above daidzein derivative or pharmaceutically acceptable salt thereof. The pharmaceutical composition of the present invention uses the daidzein derivative or pharmaceutically acceptable salt, preferably hydrochloride, as an active ingredient, and may be made into tablets, pills, powders, granules, capsules, syrups, emulsions and other chemical preparations well known to those skilled in the art. The pharmaceutical composition may further comprise a pharmaceutically acceptable carrier well known to those skilled in the art, such as excipient, adhesive, disintegrating agent, flavoring agent, deodorant, emulsifying agent, diluent, cosolvent, etc., which is not particularly limited in the present invention.

In still another aspect, the present invention provides a use of the above daidzein derivative or pharmaceutically acceptable salt thereof and pharmaceutical composition in the preparation of a drug for treating a cardiovascular disease; preferably, the cardiovascular disease is hypertension, cardiac insufficiency, stable or unstable angina, peripheral and cardiac vascular disease, arrhythmia, thromboembolic disease and local ischemia, and disease need to improve or enhance the ability of bearing hypoxia; wherein the local ischemia is preferably myocardial infarction, stroke, transient ischemic attack, peripheral circulation disease, arteriosclerosis or fibrotic disease.

Compared with the prior art, the daidzein derivative of the present invention has better therapeutic effect for cardiovascular diseases, the pharmaceutically acceptable salt of the daidzein derivative, especially the hydrochloride of the daidzein derivative, has a higher solubility.

DETAILED DESCRIPTION OF THE EMBODIMENTS

The present invention will be illustrated with reference to the specific examples. Those skilled in the art will appreciate that these examples are only intended to illustrate the present invention without limiting the scope of the present invention in any way.

The experimental methods in the following examples are all conventional methods unless expressly stated; the experimental materials used in the following examples are all purchased from conventional biochemical reagent stores unless expressly stated.

Example 1

Preparation of 7-O-chloroacetyl daidzein 10.0 g daidzein and 25 ml anhydrous pyridine were dissolved in 400 ml acetone to obtain a first mixed solution, and the first mixed solution was stirred mechanically and maintained at 0° C., and then added slowly with 27.3 chloroacetyl chloride dropwise, after completion of dropping, the first mixed solution was kept at 0° C. and continued to react for 2 h, and then warmed naturally to room temperature and continued to react for 2 h, and then the first mixed solution was sampled and detected by TLC (V (petroleum ether):V (ethyl acetate)=1:1), the result of detection indicated that the reaction was complete.

The mixture after the reaction was filtered, and the filter cake was washed with water to make the pH value achieve pH=7.0, and then dried under vacuum to give 12.0 g 7-O-chloroacetyl daidzein, with a yield of 93%.

The reaction route is as follows:

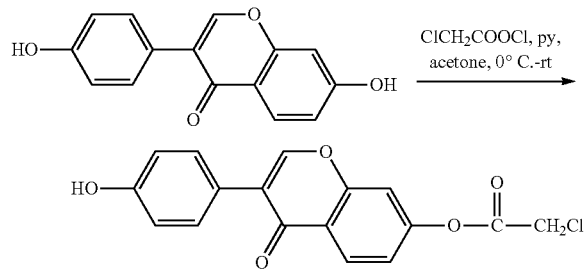

Example 2

Preparation of 7-O—N,N-diethyl-aminoacetyl daidzein hydrochloride

At room temperature, 8.8 g 7-O-chloroacetyl daidzein prepared in Example 1, 12.0 g potassium carbonate and 10.0 g potassium iodide were dissolved in 300 ml acetone, and the mixture was stirred mechanically and then added with 20 ml diethylamine, and then the resulting mixture was heated to 80° C. and reflux was performed for 4 h, TLC (V (petroleum ether):V (ethyl acetate)=1:1) indicated that the reaction was complete. The mixture was cooled, filtered and washed by acetone during filtration, and the filtrates were combined, washed and concentrated, then added with 20 ml acetone and continued to be distillated until no liquid is contained thereinto, then added with 40 ml anhydrous ethanol and 6.0 g anhydrous sodium sulfate and dried overnight. Filter, introduce dry HCl gas into the filtrate until no solid was precipitated. The mixture was filtered and recrystallized with anhydrous ethanol, and dried under vacuum to give 8.6 g solid of white powder, with a yield of 80%.

$^1$HNMR (400 MHz, d$^6$-DMSO): 10.65 (s, 1H, H-4'), 8.46 (s, 1H, H-2), 7.98 (d, 1H, J=8.8 Hz), 7.68 (d, 2H, J=8.6 Hz, H-2', H-6'), 7.32 (d, 2H, J=8.6 Hz, H3', H-5'), 6.97-7.02 (m, 2H, H-6, H-8), 4.52 (s, 2H, NCH2C=O), 3.31 (q, 4H, J=7.2 Hz, —CH$_2$CH$_3$), 1.30 (t, 6H, J=7.2 Hz, —CH$_2$CH$_3$). ESI-MS: m/z=368.15 [M+1]$^+$, 406.10[M+39]$^+$.

The reaction route is as follows:

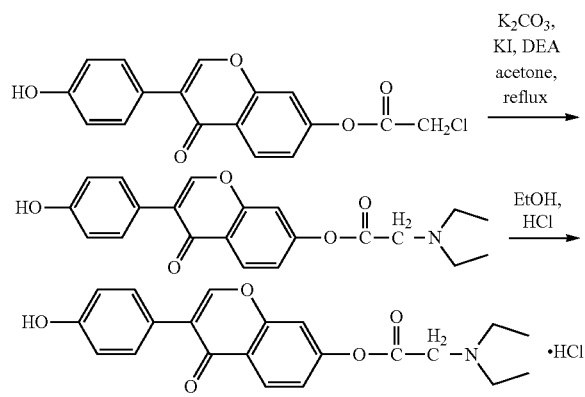

Example 3

Lyophilized powder of 7-O—N,N-diethyl-aminoacetyl daidzein hydrochloride

Prescription:

| | |
|---|---|
| Sample of Example 2 | 1.046 g |
| Sodium bicarbonate | 175 mg |
| Sodium hydroxide | 40 mg |
| Water for injection | q.s. |

The preparation process based on the prescription is as follows:

first, sodium bicarbonate and sodium hydroxide in an amount based on the above prescription were weighed and dissolved in water for injection, cooled to below 5° C. through an ice-water bath, and then the sample of Example 2 in an amount based on the above prescription was added and dissolved, and the pH value of the mixture was adjusted to 7.5 through sodium hydroxide solution, filtered and lyophilized to obtain the lyophilized powder.

Example 4

Experiment of Solubility

Experimental Materials:
7-O-chloroacetyl daidzein prepared in Example 1;
7-O—N,N-diethyl-aminoacetyl daidzein prepared in Example 2;
7-O—N,N-diethyl-aminoacetyl daidzein hydrochloride prepared in Example 2;
daidzein;

in the water bath at 25±5° C., the solvent equilibrium experiment was performed on the above materials for at least 20 hours by using 1 mL methanol, then the solution was filtered and dried in the air for 10 minutes, and after the solvent was evaporated under vacuum, the approximate solubilities of the above materials in the solvent was measured through gravimetric analysis, with results shown in table 1.

TABLE 1

| | Results of solvent equilibrium experiment at 25° C. | | | |
|---|---|---|---|---|
| Solvent | 7-O-chloroacetyl daidzein (mg/g) | 7-O-N,N-diethyl-aminoacetyl daidzein (mg/g) | 7-O-N,N-diethyl-aminoacetyl daidzein hydrochlorid (mg/g) | Daidzein (mg/g) |
| Methanol | 17.6 | 16.3 | 25 | 16.8 |

It can be seen from the results of table 1 that 7-O—N,N-diethyl-aminoacetyl daidzein hydrochloride prepared in the present invention has a higher solubility.

Example 5

Pharmacological Experiment

I. Experiment 1—Anti-Thrombosis Experiment of 7-O—N,N-diethyl-aminoacetyl daidzein hydrochloride i) Tested drug: lyophilized powder prepared in Example 3, which is dissolved with distilled water when administered in vivo, and dissolved with saline when administered in vitro, and respectively prepared into solutions with desired concentrations.

ii) Experimental animals: Wistar, which is a male rat outbreeding closed system, purchased from the Institute of Laboratory Animal Sciences, Chinese Academy of Medical Sciences, weighing 242±11.2 g, the animals are divided into 5 groups with 10 animals in each group.

iii) Experimental method:

1. Rat in vitro general artery-jugular vein blood flow in the bypass method (please refer to "Journal of Changchun University of Traditional Chinese Medicine", 2011, Volume 27, Issue 4, Pages 514-518, Yunfei Sun, Min Shi, "Study on the Effect of Pueraria Injection on Thrombosis Formation, Cerebral Ischemia and Platelet Aggregation in Rats);

2. In vitro thrombosis instrument method (please refer to "ACTA ACADEMIAE MEDICINAE PRIMAE SHANGHAI", 1979, Volume 6, Issue 3, Pages 205-206, Chengzhu Li, Shichun Yang, Fengdi Zhao, "Simple in vitro thrombosis apparatus and measuring method").

iv) Dose design, calculated according to the effective dose of 7-O—N,N-diethyl-aminoacetyl daidzein hydrochloride:

1. Experiment in vivo: the dose is 50 mg/kg, 100 mg/kg, 200 mg/kg, and the animals are administered intragastrically once daily at 1 ml/100 g mouse for 3 consecutive days;

2. Experiment in vitro: the dose is 1.56 mg/kg, 3.12 mg/kg, 6.25 mg/kg, and the animals are administered once directly.

v) Experimental control:

1. Blank control, the animals are administered with the same volume of distilled water in the experiment in vivo; and administered with the same volume of saline in the experiment in vitro;

2. Positive control, the animals are administered with acetylsalicylic acid (produced by Northwest Second Synthetic Pharmaceutical Factory) at 45 mg/kg in the experiment in vivo.

vi) Experimental results:

The antithrombotic effects of 7-O—N,N-diethyl-aminoacetyl daidzein hydrochloride are shown in table 2 and table 3:

TABLE 2

Effects on rat in vitro thrombosis after oral administration of the drug of the present invention (X ± S)

| Groups | Doses mg/kg | Wet weights of thrombus (mg) | Thrombosis inhibition rates (%) |
|---|---|---|---|
| Saline group | | 30.18 ± 3.12 | |
| High dose group | 200 | 13.79 ± 4.23** | 54.35 |
| Middle dose group | 100 | 17.89 ± 3.08* | 34.68 |
| Low dose group | 50 | 21.75 ± 3.58* | 22.36 |
| Acetylsalicylic acid group | 45 | 11.38 ± 1.47** | 58.69 |

*represents P < 0.05 compared with saline;
**represents P < 0.01 compared with saline, n = 10.

TABLE 3

Effects on whole blood in vitro thrombosis of normal rats after in vitro administration of the drug of the present invention (X ± S)

| Groups | Doses mg/kg | Wet weights of thrombus (mg) | Thrombosis inhibition rates (%) |
|---|---|---|---|
| Saline group | | 36.5 ± 3.75 | |
| High dose group | 6.25 | 10.26 ± 3.25** | 69.58 |
| Middle dose group | 3.125 | 17.41 ± 3.56* | 50.58 |
| Low dose group | 1.56 | 25.54 ± 3.42* | 27.56 |
| Acetylsalicylic acid group | 1.46 | 23.45 ± 1.28** | 32.15 |

*represents P < 0.05 compared with saline;
**represents P < 0.01 compared with saline, n = 10.

It can be seen from the results of table 2 and table 3 that 7-O—N,N-diethyl-aminoacetyl daidzein hydrochloride prepared by the present invention has a good antithrombotic effect.

II. Experiment 2—Effects of Compounds on Hypoxia Tolerance of Mice at Normal Pressure Experimental Materials:

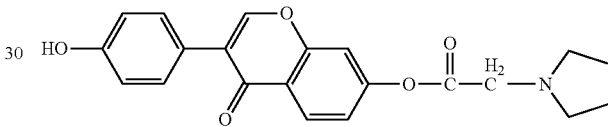

Compound of the example of the present application

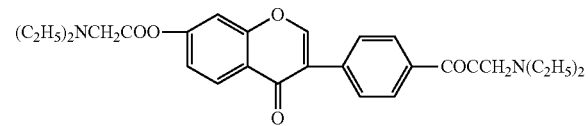

4,7-disubstituted daidzein

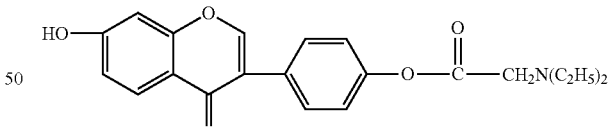

4-substituted daidzein

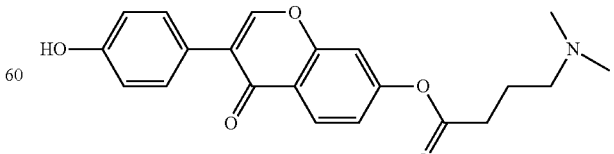

Compound in U.S. Pat. No. 6,121,010A (hereinafter referred to as "USP compound")

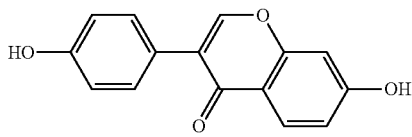 [SMILES: O=c1c(-c2ccc(O)cc2)coc2cc(O)ccc12]

Pueraria Daidzein 70 mice were taken and randomly divided into seven groups, except the blank group which was not administered and the saline group which was administered with the same volume of saline, the remaining five groups were respectively injected intraperitoneally with 25 mg/kg pueraria daidzein, 36 mg/kg compound of the example of the present application, 47 mg/kg 4,7-disubstituted daidzein, 36 mg/kg 4-substituted daidzein and 36 mg/kg USP compound (the converted dose of each compound is equivalent to the dose of the daidzein, since the daidzein is difficult to dissolve in water, 50% propylene glycol aqueous solution is used to dissolve, and other compounds were dissolved with water to achieve a suitable concentration), 20 min after administration, the mice were put into a 250 ml grinding jar (where 10 g soda lime was placed), with one mouse in each jar, and the jar was capped tightly after the mouse was put into the jar, then the survival time of the mice was immediately recorded by a stopwatch. The results are shown in table 4.

TABLE 4

Effects of various compounds on survival time of mice with hypoxia tolerance at normal pressure

| Groups | Doses (mg/kg) | Numbers of animals | Survival times (X ± s), min | Prolongation rates (%) |
|---|---|---|---|---|
| Control group | — | 10 | 22.5 ± 2.6 | |
| Solvent group | — | 10 | 20.7 ± 3.4 | |
| Pueraria daidzein | 25 | 10 | 28.1 ± 5.3** | 24.9 |
| Compound of the example of the present application* | 36 | 10 | 35.1 ± 6.6** | 56 |
| 4,7-disubstituted daidzein | 47 | 10 | 26.1 ± 5.1* | 16 |
| 4-substituted daidzein | 36 | 10 | 21.1 ± 6.4 | — |
| USP compound | 36 | 10 | 24.6 ± 5.7 | 9.3 |

Note:
*represents P < 0.05 compared with the control group, and
**represents P < 0.01 compared with the control group.

It can be seen from the results of table 4 that the compound of the example can significantly prolong the hypoxia tolerance time of the mice, and has better effect compared with the daidzein, and the poor effect of the daidzein may be caused by incomplete absorption after administration due to its poor solubility in water. Other compounds for comparison have weak effects. This may be relevant to the fact that the compounds are difficult to be hydrolyzed into the daidzein to play an effect after entering the blood vessels.

III. Experiment 3—Effects of Compounds on Acute Cerebral Ischemia in Mice 70 mice were taken and randomly divided into seven groups, except the blank group which was not administered and the saline group which was administered with the same volume of saline, the remaining five groups were respectively injected intraperitoneally with 25 mg/kg pueraria daidzein, 36 mg/kg compound of the example of the present application, 47 mg/kg 4,7-disubstituted daidzein, 36 mg/kg 4-substituted daidzein and 36 mg/kg USP compound (the converted dose of each compound is equivalent to the dose of the daidzein, since the daidzein is difficult to dissolve in water, 50% propylene glycol aqueous solution is used to dissolve, and other compounds were dissolved with water to achieve a suitable concentration), 20 min after administration, the mice were decapitated rapidly from behind the ear, then the time starting from decapitation to the last gasp was recorded. The results are shown in table 5.

TABLE 5

Effects of various compounds on the gasping time of the decapitated mice

| Groups | Doses (mg/kg) | Numbers of animals | Gasping times (X ± s), s | Prolongation rates (%) |
|---|---|---|---|---|
| Control group | — | 10 | 18.5 ± 3.1 | |
| Solvent group | — | 10 | 17.8 ± 2.9 | |
| Pueraria daidzein | 25 | 10 | 23.1 ± 6.2* | 24.9 |
| Compound of the example of the present application* | 36 | 10 | 26.7 ± 4.8** | 44.3 |
| 4,7-disubstituted daidzein | 47 | 10 | 22.1 ± 5.6 | 19.5 |
| 4-substituted daidzein | 36 | 10 | 20.3 ± 8.1 | 9.7 |
| USP compound | 36 | 10 | 23.5 ± 7.2* | 27 |

Note:
*represents P < 0.05 compared with the control group, and
**represents P < 0.01 compared with the control group.

It can be seen from the results of table 5 that the compound of the example can significantly prolong the acute ischemia tolerance time of the mice, and has better effect compared with the daidzein, and the poor effect of the daidzein may be caused by incomplete absorption after administration due to its poor solubility in water. Other compounds for comparison have weak effects. This may be relevant to the fact that the compounds are difficult to be hydrolyzed into the daidzein to play an effect after entering the blood vessels.

IV. Experiment 4—Effects of Compounds on Euglobulin Lysis Time: Antithrombotic Effect Research 1

30 guinea pigs were taken and randomly divided into five groups, each group was administered intragastrically with 25 mg/kg pueraria daidzein, 36 mg/kg compound of the example of the present application, 47 mg/kg 4,7-disubstituted daidzein, 36 mg/kg 4-substituted daidzein, and 36 mg/kg USP compound (the converted dose of each compound is equivalent to the dose of the daidzein, since the daidzein is difficult to dissolve in water, 50% propylene glycol aqueous solution is used to dissolve, and other compounds were dissolved with water to achieve a suitable concentration), 1.5 ml blood was taken from the heart before administration, and after 7 consecutive days of administration, 1.5 ml blood was taken from the heart 30 minutes after the last administration, and put into a sodium citrate anti-cruor tube, and the plasma was separated by centrifugation, then 0.5 ml plasma was taken and added with 9 ml distilled water and 0.1 ml of 1% acetic acid solution, and the mixture was centrifugated after being refrigerated for 30 minutes, then the resulting precipitate was dissolved with 0.5 ml sodium borate buffer (pH9.0), and the dissolution time was recorded as euglobulin lysis time, it can be obtained through calculation that fibrinolytic enzyme activity (u)=10000/optimal dissolution time (min). The results are shown in table 6.

TABLE 6

Effects on euglobulin lysis time of guinea pigs

| Groups | Doses (mg/kg) | Optimal dissolution times (X ± s), min | | Fibrinolytic enzyme activities (u) | |
|---|---|---|---|---|---|
| | | Before administration | After administration | Before administration | After administration |
| Pueraria daidzein | 25 | 34.5 ± 10.1 | 27.3 ± 8.4 | 289.9 | 366.3 |
| Compound of the example of the present application* | 36 | 33.6 ± 11.1 | 20.6 ± 5.5** | 297.6 | 485.4 |
| 4,7-disubstituted daidzein | 47 | 33.1 ± 6.8 | 28.6 ± 9.1 | 302.1 | 349.6 |
| 4-substituted daidzein | 36 | 30.3 ± 9.4 | 29.3 ± 5.7 | 330.0 | 341.3 |
| USP compound | 36 | 35.5 ± 8.2 | 25.7 ± 7.7* | 281.7 | 389.1 |

Note:
*represents $P < 0.05$ compared with that before administration, and
**represents $P < 0.01$ compared with that before administration.

It can be seen from the results of table 6 that the daidzein has weak antithrombotic effect after oral administration. This is mainly because the daidzein is difficult to be adsorbed by oral administration. The compound of the example improves the solubility of the drug as well as the blood concentration, thus having significant efficacy. Other compounds have poor effects probably due to absorption, hydrolysis and other reasons.

V. Experiment 5—Antithrombotic Effect Research 2 of Compounds 30 rabbits were taken and randomly divided into five groups, each group was administered intragastrically with 15 mg/kg pueraria daidzein, 22 mg/kg compound of the example of the present application, 28 mg/kg 4,7-disubstituted daidzein, 22 mg/kg 4-substituted daidzein and 22 mg/kg USP compound (the converted dose of each compound is equivalent to the dose of the daidzein, since the daidzein is difficult to dissolve in water, 50% propylene glycol aqueous solution is used to dissolve, and other compounds were dissolved with water to achieve a suitable concentration), 2 ml blood was taken from the heart before administration, and after 7 consecutive days of administration, 2 ml blood was taken from the heart 30 minutes after the last administration, and injected immediately into the rotating ring of the thrombosis instrument, and rotated at 15-17 rpm under 37° C., and the rotating time of the thrombus alone with the ring was recorded, which is defined as thrombus formation time of fibrin, the rotation was stopped after 15 minutes, the thrombus was taken out, and the length of the thrombus was measured. The results are shown in table 7.

TABLE 7

Effects of compounds on the formation time and length of thrombus

| Groups | Doses (mg/kg) | Thrombus formation times (X ± s), min | | Lengths of thrombus (cm) | |
|---|---|---|---|---|---|
| | | Before administration | After administration | Before administration | After administration |
| Pueraria daidzein | 15 | 6.21 ± 1.23 | 7.18 ± 1.27 | 14.2 ± 1.95 | 12.8 ± 1.49* |
| Compound of the example of the present application* | 22 | 6.29 ± 1.31 | 8.17 ± 1.54** | 14.9 ± 1.27 | 10.7 ± 1.96** |
| 4,7-disubstituted daidzein | 28 | 6.17 ± 1.64 | 7.16 ± 1.91 | 15.1 ± 1.94 | 14.6 ± 2.24 |
| 4-substituted daidzein | 22 | 6.44 ± 1.71 | 7.25 ± 1.34 | 14.7 ± 2.02 | 14.1 ± 2.17 |
| USP compound | 22 | 6.37 ± 1.72 | 7.31 ± 1.72 | 14.1 ± 3.84 | 11.8 ± 2.01 |

Note:
*represents $P < 0.05$ compared with that before administration, and
**represents $P < 0.01$ compared with that before administration.

It can be seen from the results of table 7 that the daidzein has weak antithrombotic effect after oral administration. This is mainly because the daidzein is difficult to be adsorbed by oral administration. The compound of the example improves the solubility of the drug as well as the blood concentration, thus having significant efficacy, the thrombus formation time is significantly extended and the length of the thrombus is obviously shortened. Other compounds have poor effects probably due to absorption, hydrolysis and other reasons.

The above are detailed description of the daidzein derivative and pharmaceutically acceptable salt thereof provided by the present invention. The present invention illustrates the principle and embodiments of the present invention through specific examples, and the descriptions of the above examples are only intended to help understand the method and its core concept of the present invention. It should be noted that, those of ordinary skill in the art can make a number of improvements and modifications on the present invention, without departing from the principle of the present invention, and these improvements and modifications also fall within the protection scope of the claims of the present invention.

What is claimed is:

1. A daidzein derivative having a structure represented by formula (I) or pharmaceutically acceptable salt thereof:

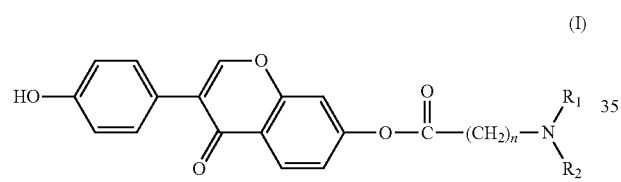

(I)

wherein $R_1$ and $R_2$ are each independently H, substituted or unsubstituted $C_{1-10}$ alkyl, or $R_1$ and $R_2$ together with the attached N atom form substituted or unsubstituted 5-10 membered heterocyclic group, and when substituted, the $C_{1-10}$ alkyl or 5-10 membered heterocyclic group has a substitute of $C_{1-10}$ alkyl, hydroxyl, carboxyl or halogen; n is 1, 2, 3, 4 or 5;

and the daidzein derivative does not comprise 7-O—N,N-dimethyl-aminobutyryl daidzein.

2. The daidzein derivative or pharmaceutically acceptable salt thereof according to claim 1, wherein $R_1$ and $R_2$ are each independently H, substituted or unsubstituted $C_{1-10}$ alkyl, wherein when substituted, the $C_{1-10}$ alkyl has a substitute of hydroxyl, carboxyl or halogen.

3. The daidzein derivative or pharmaceutically acceptable salt thereof according to claim 1, wherein n is 1, 2 or 3.

4. The daidzein derivative or pharmaceutically acceptable salt thereof according to claim 1, wherein the pharmaceutically acceptable salt is a salt formed by the daidzein derivative having a structure represented by formula (I) and an organic acid or inorganic acid.

5. The daidzein derivative or pharmaceutically acceptable salt thereof according to claim 1, wherein the daidzein derivative has a structure as shown in formula (II):

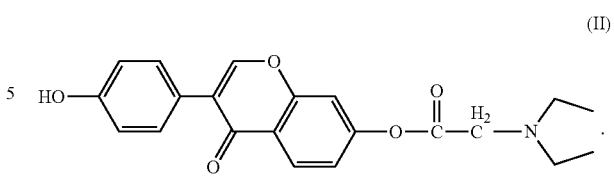

(II)

6. A method for preparing the daidzein derivative or pharmaceutically acceptable salt thereof according to claim 1, comprising the following steps:

a) reacting daidzein and halogenated alkyl acyl halide to obtain halogenated alkyl acyl daidzein:

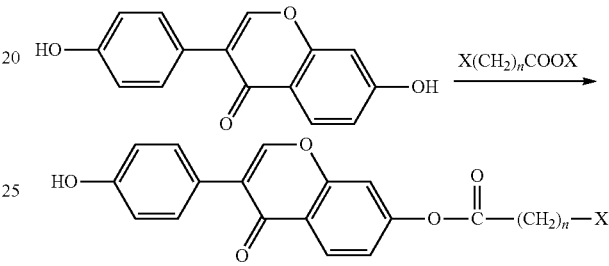

wherein X is halogen;

b) reacting the halogenated alkyl acyl daidzein and amine represented by formula (IV) to obtain the daidzein derivative:

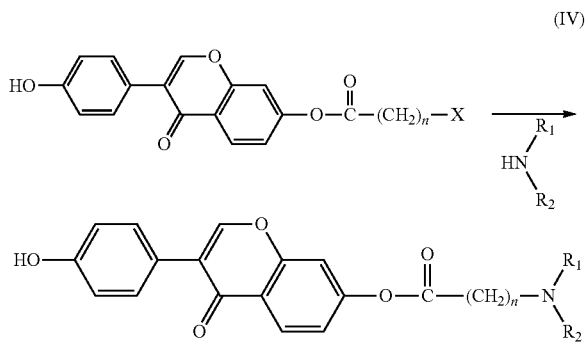

(IV)

and c) optionally, converting the daidzein derivative into its pharmaceutically acceptable salt.

7. The method according to claim 6, wherein the step a) comprises:

reacting daidzein and halogenated alkyl acyl halide with pyridine as a catalyst in a first organic solvent to obtain halogenated alkyl acyl daidzein.

8. The method according to claim 6, wherein the step b) comprises:

dissolving the halogenated alkyl acyl daidzein obtained in the step a) in a second organic solvent, adding potassium carbonate and potassium iodide, and then adding

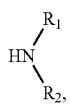

heating to reflux, to obtain the daidzein derivative through reaction.

9. The method according to claim 6, wherein the step c) comprises:
dissolving the daidzein derivative obtained in the step b) in a third organic solvent, then adding an organic or inorganic acid, so that the daidzein derivative can react with the acid to form a pharmaceutically acceptable salt of the daidzein derivative.

10. A pharmaceutical composition comprising the daidzein derivative or pharmaceutically acceptable salt thereof according to claim 1 and optionally a pharmaceutically acceptable carrier.

11. The daidzein derivative or pharmaceutically acceptable salt thereof according to claim 1, wherein $R_1$ and $R_2$ are each independently H or unsubstituted $C_{1-10}$ alkyl; wherein the $C_{1-10}$ alkyl is $C_{1-6}$ alkyl.

12. The daidzein derivative or pharmaceutically acceptable salt thereof according to claim 1, wherein $R_1$ and $R_2$ are each independently H or unsubstituted $C_{1-10}$ alkyl; wherein the $C_{1-10}$ alkyl is $C_{1-4}$ alkyl.

13. The daidzein derivative or pharmaceutically acceptable salt thereof according to claim 4, wherein the organic acid is selected from the group consisting of acetic acid, trifluoroacetic acid, methane sulfonic acid, toluene sulfonic acid, maleic acid, succinic acid, tartaric acid, citric acid and fumaric acid; the inorganic acid is selected from the group consisting of hydrochloric acid, hydrobromic acid, nitric acid, sulfuric acid and phosphoric acid.

14. The daidzein derivative or pharmaceutically acceptable salt thereof according to claim 1, wherein the pharmaceutically acceptable salt is a hydrochloride having a structure as shown in formula (III):

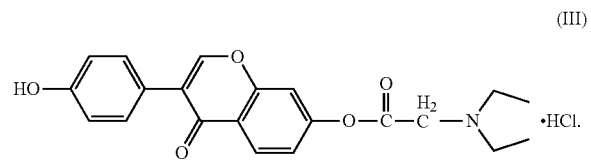 [SMILES: CCN(CC)CC(=O)Oc1ccc2c(=O)c(-c3ccc(O)cc3)coc2c1]

15. The method according to claim 7, wherein the first organic solvent is an organic solvent of alcohols, halogenated hydrocarbons, ethers, ketones or esters, or a mixture thereof; wherein the organic solvent of alcohols is one or more selected from the group consisting of methanol, ethanol, isopropanol, n-propanol, n-butanol and t-butanol; the organic solvent of halogenated hydrocarbons is one or more selected from the group consisting of dichloromethane, chloroform and 1,2-dichloroethylene; the organic solvent of ethers is one or more selected from the group consisting of tetrahydrofuran, diethyl ether, isopropyl ether, anisole and methyl tertiary butyl ether; the organic solvent of ketones is one or more selected from the group consisting of acetone, methyl isobutyl ketone, butanone and methyl n-butyl ketone; the organic solvent of esters is one or more selected from the group consisting of ethyl acetate, isobutyl acetate, butyl acetate and isopropyl acetate.

16. The method according to claim 7, wherein the first organic solvent is acetone.

17. The method according to claim 7, wherein during the reaction of the daidzein and halogenated alkyl acyl halide, the reaction temperature is 0° C.-25° C.

18. The method according to claim 7, wherein during the reaction of the daidzein and halogenated alkyl acyl halide, the reaction temperature is 1° C.-15° C.

19. The method according to claim 7, wherein during the reaction of the daidzein and halogenated alkyl acyl halide, the reaction temperature is 2° C.-5° C.

20. The method according to claim 7, wherein during the reaction of the daidzein and halogenated alkyl acyl halide, the reaction time is 1 h-10 h.

21. The method according to claim 7, wherein during the reaction of the daidzein and halogenated alkyl acyl halide, the reaction time is 2 h-8 h.

22. The method according to claim 7, wherein during the reaction of the daidzein and halogenated alkyl acyl halide, the reaction time is 3 h-7 h.

23. The method according to claim 7, wherein the mass ratio of the daidzein and halogenated alkyl acyl halide is 1:10-2:5.

24. The method according to claim 7, wherein the mass ratio of the daidzein and halogenated alkyl acyl halide is 1:8-3:6.

25. The method according to claim 7, wherein the concentration of the daidzein in the first organic solvent is 0.05 mol/l-0.2 mol/l.

26. The method according to claim 7, wherein the concentration of the daidzein in the first organic solvent is 0.08 mol/l-0.18 mol/l.

27. The method according to claim 7, wherein the concentration of the daidzein in the first organic solvent is 0.09 mol/l-0.15 mol/l.

28. The method according to claim 7, wherein the concentration of the daidzein in the first organic solvent is 0.1 mol/l-0.12 mol/l.

29. The method according to claim 8, wherein the second organic solvent is an organic solvent of alcohols, halogenated hydrocarbons, ethers, ketones or esters, or a mixture thereof; wherein the organic solvent of alcohols is one or more selected from the group consisting of methanol, ethanol, isopropanol, n-propanol, n-butanol and t-butanol; the organic solvent of halogenated hydrocarbons is one or more selected from the group consisting of dichloromethane, chloroform and 1,2-dichloroethylene; the organic solvent of ethers is one or more selected from the group consisting of tetrahydrofuran, diethyl ether, isopropyl ether, anisole and methyl tertiary butyl ether; the organic solvent of ketones is one or more selected from the group consisting of acetone, methyl isobutyl ketone, butanone and methyl n-butyl ketone; the organic solvent of esters is one or more selected from the group consisting of ethyl acetate, isobutyl acetate, butyl acetate and isopropyl acetate.

30. The method according to claim 8, wherein the second organic solvent is identical to the first organic solvent in the step a).

31. The method according to claim 8, wherein the second organic solvent is acetone.

32. The method according to claim 8, wherein the time for reflux reaction is at least 1 h.

33. The method according to claim 8, wherein the time for reflux reaction is at least 2 h.

34. The method according to claim 8, wherein the time for reflux reaction is at least 3 h.

35. The method according to claim 9, wherein the adding of an organic or inorganic acid comprises passing through dry HCl gas or adding hydrochloric acid, and further comprising performing filtration and concentration to obtain a hydrochloride of the daidzein derivative.

36. The method according to claim 9, wherein the third organic solvent is an organic solvent of alcohols, halogenated hydrocarbons, ethers, ketones or esters, or a mixture thereof; wherein the organic solvent of alcohols is one or more selected from the group consisting of methanol, ethanol, isopropanol, n-propanol, n-butanol and t-butanol; the organic solvent of halogenated hydrocarbons is one or more selected from the group consisting of dichloromethane, chloroform and 1,2-dichloroethylene; the organic solvent of ethers is one or more selected from the group consisting of tetrahydrofuran, diethyl ether, isopropyl ether, anisole and methyl tertiary butyl ether; the organic solvent of ketones is one or more selected from the group consisting of acetone, methyl isobutyl ketone, butanone and methyl n-butyl ketone; the organic solvent of esters is one or more selected from the group consisting of ethyl acetate, isobutyl acetate, butyl acetate and isopropyl acetate.

37. The method according to claim 9, wherein the third organic solvent is identical to the first organic solvent in the step a).

38. The method according to claim 9, wherein the third organic solvent is methanol.

39. The pharmaceutical composition according to claim 10, wherein the pharmaceutically acceptable carrier is one or more selected from the group consisting of excipient, adhesive, disintegrating agent, flavoring agent, deodorant, emulsifying agent, diluent and cosolvent.

40. A method for treating a cardiovascular disease, the method comprising:
    administering a drug comprising the daidzein derivative or pharmaceutically acceptable salt thereof according to claim 1 to a patient.

* * * * *